(12) United States Patent
Arigoni et al.

(10) Patent No.: US 8,454,949 B2
(45) Date of Patent: Jun. 4, 2013

(54) *LACTOBACILLUS HELVETICUS* CNCM I-4095 AND WEIGHT CONTROL

(75) Inventors: Fabrizio Arigoni, Tokyo (JP); Christian Darimont-Nicolau, Lausanne (CH); Catherine Mace, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/147,687

(22) PCT Filed: Feb. 4, 2010

(86) PCT No.: PCT/EP2010/051360
§ 371 (c)(1),
(2), (4) Date: Aug. 3, 2011

(87) PCT Pub. No.: WO2010/091991
PCT Pub. Date: Aug. 19, 2010

(65) Prior Publication Data
US 2011/0293568 A1 Dec. 1, 2011

(30) Foreign Application Priority Data
Feb. 10, 2009 (EP) .................................. 09152434

(51) Int. Cl.
*A01N 63/00* (2006.01)
*C12N 1/20* (2006.01)

(52) U.S. Cl.
USPC .................... 424/93.3; 424/93.45; 435/252.9

(58) Field of Classification Search
None
See application file for complete search history.

(56) References Cited

U.S. PATENT DOCUMENTS

| | | | |
|---|---|---|---|
| 2005/0100617 A1* | 5/2005 | Malnoe et al. | 424/728 |
| 2005/0153018 A1* | 7/2005 | Ubbink et al. | 426/61 |
| 2006/0099321 A1* | 5/2006 | Sievert | 426/618 |
| 2006/0251633 A1* | 11/2006 | Salvadori et al. | 424/93.45 |
| 2007/0128178 A1* | 6/2007 | Corthesy-Theulaz et al. | 424/93.45 |

FOREIGN PATENT DOCUMENTS

| | | |
|---|---|---|
| DK | EP1820849 | 4/2009 |
| EP | 1974734 | 1/2008 |
| EP | 2062587 | 5/2009 |
| WO | WO2007096498 | 8/2007 |
| WO | W02007119693 | 10/2007 |
| WO | W02008029505 | 3/2008 |

* cited by examiner

Primary Examiner — Chris R Tate
Assistant Examiner — Douglas F White
(74) Attorney, Agent, or Firm — K&L Gates LLP

(57) ABSTRACT

The present invention generally relates to the field of obesity. In particular the present invention relates to the use of probiotics to support weight management and to treat or prevent obesity. One embodiment of the present invention relates to the use of *Lactobacillus helveticus* CNCM I-4095 for the preparation of a composition to support weight management, promote weight loss and/or to treat obesity.

33 Claims, 1 Drawing Sheet

LACTOBACILLUS HELVETICUS CNCM I-4095 AND WEIGHT CONTROL

The present invention generally relates to the field of weight management. In particular the present invention relates to the use of probiotics to support weight management, promote weight loss and/or to treat obesity.

During the past decades, the prevalence of obesity has increased worldwide to epidemic proportion. Approximately 1 billion of people worldwide are overweight or obese, conditions that increase mortality, mobility and economical costs. Obesity develops when energy intake is greater than energy expenditure, the excess energy being stored mainly as fat in adipose tissue. Body weight loss and prevention of weight gain can be achieved by reducing energy intake or bioavailability, increasing energy expenditure and/or reducing storage as fat. Obesity represents a serious threat to health because it is associated with an array of chronic diseases, including diabetes, atherosclerosis, degenerative disorders, airway diseases and some cancers.

Modifications of the intestinal flora were recently associated with obesity. These changes were demonstrated in obese mice to affect the metabolic potential of gut microbiota resulting in an increased capacity to harvest energy from the diet (Turnbaugh P J, Ley R E, Mahowald M A, Magrini V, Mardis E R, Gordon J I. An obesity-associated gut microbiome with increased capacity for energy harvest. Nature. 2006; Ley R E, Turnbaugh P J, Klein S, Gordon J I. Microbial ecology: human gut microbes associated with obesity. Nature. 2006). Such modifications of gut microbiota are proposed to contribute to the pathophysiology of obesity. Probiotics, the beneficial bacteria present in food or food supplements, are known to modify the intestinal microbiota (Fuller R & Gibson G R. Modification of the intestinal microflora using probiotics and prebiotics. Scand J. Gastroenterol. 1997).

There remains to be a need in the art to identify specific species of probiotic bacteria that exhibit a beneficial effect on weight management and obesity and may be used to treat or prevent metabolic disorders.

With this in mind, it would further be desirable, if theses species were already used in the food industry today, so that the necessary know-how on how to handle a specific probiotic species in industrial scale was already available.

It would also be a helpful, if the identified species also had a taste that the consumers perceive as pleasant, so that no manufacturing steps are required to mask a potentially unpleasant taste of a probiotic species.

WO 2007119693 teaches that an extract of the *Lactobacillus helveticus* ATCC 1120 strain obtained with an organic solvent can be used to activate a peroxisome proliferator-activated receptor (PPAR) to thereby improve the lipid metabolism. The authors of this document see improving the lipid metabolism as a tool for the treatment, prevention or amelioration of diabetes, hyperlipemia or obesity.

However, the use of organic solvents may problematic in the food industry. Often times, organic solvents must be removed completely, before an ingredient can be added to a food product. In any case, the requirement of an extraction step complicates the manufacturing and increases costs.

Based on this prior art it was the object of the present invention to identify further species of probiotic bacteria that may be used without prior extraction steps and that offer an attractive effectiveness that can be used to treat obesity and that overcomes disadvantages of the strains of the prior art.

This object is achieved by the use of claim 1.

The present inventors have found that—unexpectedly—the species *Lactobacillus helveticus*, in particular the strain *Lactobacillus helveticus* NCC 2849 achieves this object.

It was found that these probiotic bacteria—advantageously—may be used without prior extraction steps, in particular extraction steps involving organic solvents.

*Lactobacillus helveticus* is a lactic-acid producing rod shaped bacterium of the genus *Lactobacillus*. Today, it is commonly used in the food industry, for example in the manufacturing of Emmental cheese but is also sometimes used in making other styles of cheese, such as Cheddar, Parmesan, romano, provolone, and mozzarella. Importantly, the use of *Lactobacillus helveticus* is known to prevent bitterness and—at the same time—produces pleasant nutty flavours in the final cheese.

*Lactobacillus helveticus* NCC 2849 was deposited on Dec. 2, 2008 under the Budapest treaty with the Collection Nationale de Cultures de Microorganism, Institut Pasteur, 25, Rue du Docteur Roux, F-76724 Paris Cedex 15, and assigned accession number CNCM I-4095.

Hence, one embodiment of the present invention is the use of *Lactobacillus helveticus*, in particular *Lactobacillus helveticus* CNCM I-4095, for the preparation of a composition to treat obesity in animals.

A further embodiment of the present invention is the use of *Lactobacillus helveticus*, in particular *Lactobacillus helveticus* CNCM I-4095, for the preparation of a composition to promote weight loss.

A further embodiment of the present invention is the use of *Lactobacillus helveticus*, in particular *Lactobacillus helveticus* CNCM I-4095, for the preparation of a composition to reduce caloric intake and/or to increase satiety.

Still, a further embodiment of the present invention is the use of *Lactobacillus helveticus*, in particular *Lactobacillus helveticus* CNCM I-4095, for the preparation of a composition to support weight management.

The compositions described in the framework of the present invention are in particular beneficial for long term applications. The inventors have shown in an animal model that a mouse treated with the composition described in the present invention will put on significantly less weight than a control mouse if fed a high caloric diet. This effect was the more pronounced the longer the composition was administered. The experiment was continued for about two months and the observed effects increased with time.

Consequently, in a preferred embodiment of the present invention, the composition is to be administered for at least 2 weeks, at least 3 weeks, at least 4 weeks, at least 5 weeks, at least 6 weeks, at least 7 weeks, and/or at least 8 weeks.

In this specification, the following terms have the following meanings:

"Animal" means animals including humans.

The term "*Lactobacillus helveticus* CNCM I-4095" is meant to include the bacterium, a cell growth medium with the bacterium or a cell growth medium in which *Lactobacillus helveticus* CNCM I-4095 was cultivated. *Lactobacillus helveticus* CNCM I-4095 may be present as viable bacteria, as non-replicating bacteria, or as a mixture thereof.

"Body mass index" or "BMI" means the ratio of weight in Kg divided by the height in metres, squared.

"Overweight" is defined for an adult human as having a BMI between 25 and 30.

"Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

"Probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

"Prebiotic" means food substances intended to promote the growth of probiotic bacteria in the intestines.

"Food grade bacteria" means bacteria that are used and generally regarded as safe for use in food.

"Weight loss" in the context of the present invention is a reduction of the total body weight. Weight loss may for example refer to the loss of total body mass in an effort to improve fitness, health, and/or appearance.

"Weight management" or "weight maintenance" relates to maintaining a total body weight. For example, weight management may relate to maintaining a BMI in the area of 18, 5-25 which is considered to be normal.

The composition of the present invention may further contain protective hydrocolloids (such as gums, proteins, modified starches), binders, film forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, anti-oxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

The composition may be a nutritionally complete formula.

The composition according to the invention may comprise a source of protein.

Any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred.

The proteins may be intact or hydrolysed or a mixture of intact and hydrolysed proteins. It may be desirable to supply partially hydrolysed proteins (degree of hydrolysis between 2 and 20%), for example for animals believed to be at risk of developing cows' milk allergy. If hydrolysed proteins are required, the hydrolysis process may be carried out as desired and as is known in the art. For example, a whey protein hydrolysate may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also contain a source of carbohydrates and a source of fat.

If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil.

A source of carbohydrates may be added to the composition.

The source of carbohydrates preferably provides about 40% to 80% of the energy of the composition. Any suitable carbohydrate may be used, for example sucrose, lactose, glucose, fructose, corn syrup solids, maltodextrins, and mixtures thereof. Dietary fibre may also be added if desired. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. A preferred fibre blend is a mixture of inulin with shorter chain fructo-oligosaccharides. Preferably, if fibre is present, the fibre content is between 2 and 40 g/l of the composition as consumed, more preferably between 4 and 10 g/l.

The composition may also contain minerals and micronutrients such as trace elements and vitamins in accordance with the recommendations of Government bodies such as the USRDA One or more food grade emulsifiers may be incorporated into the composition if desired; for example diacetyl tartaric acid esters of mono- and di-glycerides, lecithin and mono- and di-glycerides. Similarly suitable salts and stabilisers may be included.

The composition is preferably orally or enterally administrable; for example in the form of a powder for re-constitution with milk or water.

Preferably, the composition is provided in the form of a powder, e.g., a shelf stable powder. Shelf stability can be obtained, for example by providing the composition with a water activity smaller than 0.2, for example in the range of 0.19-0.05, preferably smaller than 0.15.

Water activity or $a_w$ is a measurement of the energy status of the water in a system. It is defined as the vapour pressure of water divided by that of pure water at the same temperature; therefore, pure distilled water has a water activity of exactly one.

The composition described above may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

Lactobacillus helveticus CNCM I-4095 may be cultured according to any suitable method and prepared for addition to the composition by freeze-drying or spray-drying for example. Appropriate culturing methods for Lactobacillus helveticus CNCM I-4095 are known to those skilled in the art. Alternatively, bacterial preparations can be bought from specialist suppliers such as Christian Hansen and Danisco already prepared in a suitable form for addition to food products such as nutritional and infant formulas. The probiotic bacteria may be added to the formula in an appropriate amount, preferably between $10^2$ and $10^{12}$ cfu/g powder, more preferably between $10^7$ and $10^{12}$ cfu/g powder.

In one embodiment of the present invention the animals to be treated with the composition prepared by the use of the present invention are at least two years old. This age limit applies in particular to humans. If the animals to be treated with the composition prepared by the use of the present invention are dogs or cats, for example, the dog or cat should be at least 4 months old.

In one embodiment of the present invention the composition is a medicament. As a medicament the dosage of Lactobacillus helveticus CNCM I-4095 can be carefully adjusted according to a doctor's recommendation.

The composition prepared according to the present may also be a food product. As a food product the beneficial effects of Lactobacillus helveticus CNCM I-4095 would be available to everyone. Lactobacillus helveticus CNCM I-4095 could thus be easily used by everybody to support weight management. Treatment or prevention of obesity could be initiated at a much earlier stage. Further, in a food product Lactobacillus helveticus CNCM I-4095 would be even more pleasant to consume. Examples of food products that are applicable to the present invention are yoghurts, milk, flavoured milk, ice cream, ready to east desserts, powders for re-constitution with, e.g., milk or water, chocolate milk drinks, malt drinks, ready-to-eat dishes, instant dishes or drinks for humans or food compositions representing a complete or a partial diet intended for pets or livestock.

Consequently, in one embodiment the composition according to the present invention is a food product intended for humans, pets or livestock. In particular the composition is intended for animals selected from the group consisting of dogs, cats, pigs, cattle, horses, goats, sheep, poultry. In a preferred embodiment is the composition a food product intended for adult species, in particular human adults.

The composition of the present invention may also comprise at least one other kind of other food grade bacteria or yeast. The food grade bacteria may be probiotic bacteria and are preferably selected from the group consisting of lactic acid bacteria, bifidobacteria, propionibacteria or mixtures thereof. Probiotic bacteria may be any lactic acid bacteria or Bifidobacteria with established probiotic characteristics. For example they may be also capable of promoting the development of a bifidogenic intestinal microbiota. Suitable probiotic Bifidobacteria strains include Bifidobacterium lactis CNCM I-3446 sold inter alia by the Christian Hansen company of Denmark under the trade mark Bb12, Bifidobacterium longum ATCC BAA-999 sold by Morinaga Milk Industry Co. Ltd. of Japan under the trade mark BB536, the strain of Bifidobacterium breve sold by Danisco under the trade mark Bb-03, the strain of Bifidobacterium breve sold by Morinaga under the trade mark M-16V and the strain of Bifidobacterium breve sold by Institut Rosell (Lallemand) under the trade mark R0070. A mixture of suitable probiotic lactic acid bacteria and Bifidobacteria may be used.

As food grade yeast the following can be used for example: Saccharomyces cerevisiae and/or Saccharomyces boulardii.

In a preferred embodiment of the present invention the composition further contains at least one prebiotic. Prebiotics can promote the growth of certain food grade bacteria, in particular of probiotic bacteria, in the intestines and can hence enhance the effect of Lactobacillus helveticus CNCM I-4095. Furthermore, several prebiotics have a positive influence on, e.g., digestion.

Preferably the prebiotic is selected from the group consisting of oligosaccharides and optionally contain fructose, galactose, mannose, soy and/or inulin; dietary fibers; or mixtures thereof.

The compositions may contain at least one prebiotic in an amount of 0.3 to 10% dry weight of the composition. Prebiotics are non-digestible food ingredients that beneficially affect the host by selectively stimulating the growth and/or activity of one or a limited number of bacteria in the colon, and thus improve host health. Such ingredients are non-digestible in the sense that they are not broken down and absorbed in the stomach or small intestine and thus pass intact to the colon where they are selectively fermented by the beneficial bacteria.

Further examples of prebiotics include certain oligosaccharides, such as fructooligosaccharides (FOS) and galactooligosaccharides (GOS). A combination of prebiotics may be used, such as 90% GOS with 10% short chain fructo-oligosaccharides such as the product sold under the trade mark Raftilose® or 10% inulin such as the product sold under the trade mark Raftiline®.

A particularly preferred prebiotic is a mixture of galacto-oligosaccharide(s), N-acetylated oligosaccharide(s) and sialylated oligosaccharide(s) in which the N-acetylated oligosaccharide(s) comprise 0.5 to 4.0% of the oligosaccharide mixture, the galacto-oligosaccharide(s) comprise 92.0 to 98.5% of the oligosaccharide mixture and the sialylated oligosaccharide(s) comprise 1.0 to 4.0% of the oligosaccharide mixture. This mixture is hereinafter referred to as "CMOS-GOS". Preferably, a composition for use according to the invention contains from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide.

Suitable N-acetylated oligosaccharides include GalNAcα-1,3Galβ1,4Glc and Galβ1,6GalNAcα-1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

Suitable galacto-oligosaccharides include Galβ1,6Gal, Galβ1,6Galβ1,4Glc Galβ1,6Galβ1,6Glc, Galβ1,3Galβ1, 3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1, 4Galβ1,4Galβ1,4Glc. Synthesised galacto-oligosaccharides such as Galβ1,6Galβ1,4Glc Galβ1,6Galβ1,6Glc, Galβ1, 3Galβ1,4Glc, Galβ1,6Galβ1,6Galβ1,4Glc, Galβ1,6Galβ1, 3Galβ1,4Glc and Galβ1,3Galβ1,6Galβ1,4Glc, Galβ1, 4Galβ1,4Glc and Galβ1,4Galβ1,4Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

Suitable sialylated oligosaccharides include NeuAcα2, 3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

One advantage of the present invention is that *Lactobacillus helveticus* CNCM I-4095 are effective, both, as living bacterium as well as inactivated bacterial species. Consequently, even conditions that will not allow the presence of living bacteria will not abolish the effectiveness of *Lactobacillus helveticus* CNCM I-4095.

It is preferred, however that at least a part of the *Lactobacillus helveticus* CNCM I-4095 are alive in the composition and preferably arrive alive in the intestine. This way they can colonize the intestine and increase their effectiveness by multiplication.

However, for special sterile food products or medicaments it might be preferable that *Lactobacillus helveticus* CNCM I-4095 are not alive in the composition. Hence, in one embodiment of the present invention at least a part of the *Lactobacillus helveticus* CNCM I-4095 are not alive in the composition.

*Lactobacillus helveticus* CNCM I-4095 will be effective in any concentration. If *Lactobacillus helveticus* CNCM I-4095 reaches the intestine alive, a single bacterium can theoretically be sufficient to achieve a powerful effect by colonization and multiplication.

However, for a medicament it is generally preferred that a daily dose of the medicament comprises between $10^2$ and $10^{12}$ cfu of *Lactobacillus helveticus* CNCM I-4095. A particular suitable daily dose of *Lactobacillus helveticus* CNCM I-4095 is from $10^5$ to $10^{11}$ colony forming units (cfu), more preferably from $10^7$ to $10^{10}$ cfu.

In the case of inactivated *Lactobacillus helveticus* CNCM I-4095 it is generally preferred that a daily dose of the medicament comprises between $10^2$ and $10^{12}$ cells of *Lactobacillus helveticus* CNCM I-4095. A particular suitable daily dose of *Lactobacillus helveticus* CNCM I-4095 is from $10^5$ to $10^{11}$ cells, more preferably from $10^7$ to $10^{10}$ cells.

For a food composition it is generally preferred that it comprises between $10^3$ and $10^{12}$ cfu of *Lactobacillus helveticus* CNCM I-4095 per g of the dry weight of the food composition. A particular suitable amount of *Lactobacillus helveticus* CNCM I-4095 is from $10^5$ to $10^{11}$ cfu per g of the dry weight of the food composition, more preferably from $10^7$ to $10^{10}$ cfu per g of the dry weight of the food composition.

In the case of inactivated *Lactobacillus helveticus* CNCM I-4095 it is generally preferred that the food composition comprises between $10^3$ and $10^{12}$ cells of *Lactobacillus helveticus* CNCM I-4095 per g of the dry weight of the food composition. A particular suitable amount of *Lactobacillus helveticus* CNCM I-4095 is from $10^5$ to $10^{11}$ cells per g of the dry weight of the food composition, more preferably from $10^7$ to $10^{10}$ cells per g of the dry weight of the food composition.

The daily dose of *Lactobacillus helveticus* CNCM I-4095 in a composition will depend on the particular person or animal to be treated. Important factors to be considered include age, body weight, sex and health condition.

For example a typical daily dose of *Lactobacillus helveticus* CNCM I-4095 in a composition will be in the range of $10^4$-$10^{12}$ cfu and/or cells per day, preferably $10^6$-$10^{10}$ cfu and/or cells per day, preferably $10^7$-$10^9$ cfu and/or cells per day.

A further use of a composition comprising *Lactobacillus helveticus* CNCM I-4095 according to the present invention is to support weight loss and/or weight maintenance.

Since establishing and maintaining a proper body weight and—in particular—an acceptable weight percentage of fat in the body is a key step to treat or prevent metabolic disorders, a further use of a composition comprising *Lactobacillus helveticus* CNCM I-4095 according to the present invention is to treat or prevent metabolic disorders.

In particular, a composition comprising *Lactobacillus helveticus* CNCM I-4095 according to the present invention can be used to treat or prevent diabetes, hypertension and/or cardiovascular diseases and can hence make a significant contribution to the well-being of today's population in a number countries, in particular, in well developed countries.

The present invention also concerns a composition comprising *Lactobacillus helveticus* CNCM I-4095 for use in the treatment or prevention of the conditions described in the present application.

It is clear to those skilled in the art that any features described in this specification can be combined freely without departing from the scope of the present invention as disclosed.

Further features and advantages of the present invention result from the following Examples and Figures.

EXAMPLE

Seven to eight weeks-old male obese ob/ob mice were fed a chow diet and treated with $10^9$-$10^{10}$ cfu *Lactobacillus hel-* veticus NCC2849 per day for 42 days. *Lactobacillus helveticus* NCC2849 biomass diluted in the culture medium was administrated in the drinking solution containing NaCl 9/1000, the control group received the saline solution with corresponding amount of culture medium present in the probiotic preparation. Body weight and energy intake were followed during the study.

Figure 1:
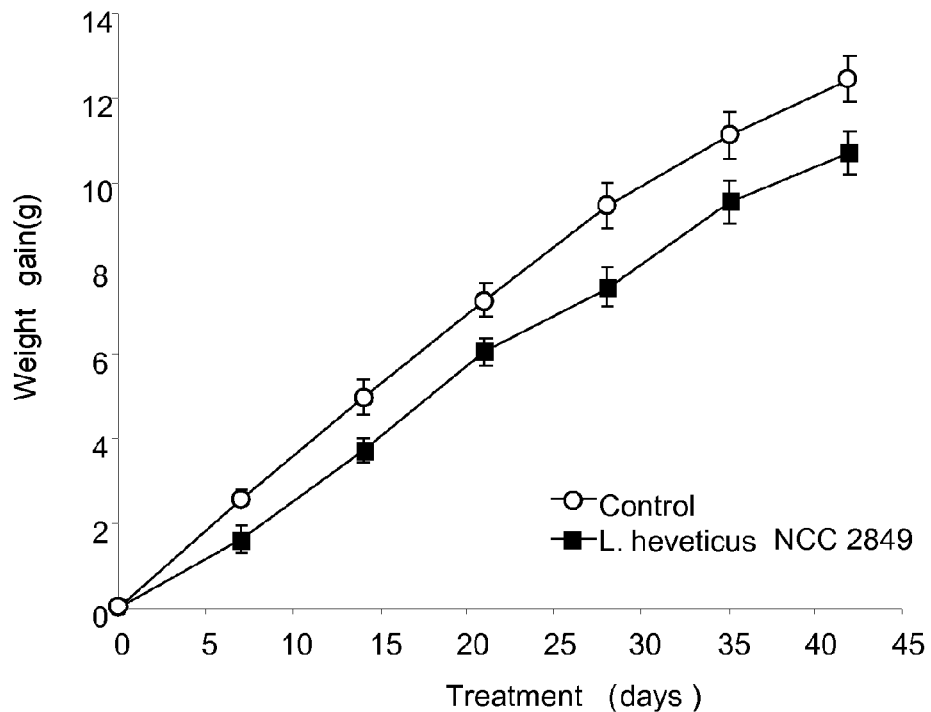
FIG. 1 shows the weight gain in the ob/ob mice treated or not with *L. helveticus* NCC2849. It is clear that long term administration (42 days) of the *Lactobacillus helveticus* NCC2849 at $10^9$-$10^{10}$ CFU per day prevents weight gain in hyperphagic obese mice (ob/ob).

Body weight gain of both obese (ob/ob) mice receiving *Lactobacillus helveticus* NCC2849 in the drinking solution was reduced by about 17% after 42 days, as compared with the control group (FIG. 1).

Figure 2:
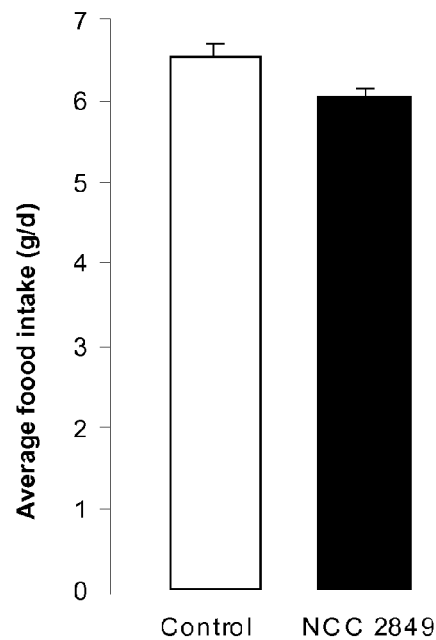
FIG. 2 shows the caloric intake of ob/ob mice treated or not with *L. helveticus* NCC2849. It is clear that the use of *L. helveticus* NCC2849 also leads to a reduction of caloric intake.

Administration of the *Lactobacillus helveticus* NCC2849 strain additionally induced a reduction of caloric intake in obese mice as compared to control animals (FIG. 2).

The invention claimed is:

1. A method for weight loss comprising the step of administering to a mammal requiring weight loss a composition comprising an effective amount of *Lactobacillus helveticus* CNCM I-4095.

2. The method in accordance with claim 1, wherein the mammal is a human that is at least 2 years old.

3. The method in accordance with claim 1, wherein the composition is selected from the group consisting of a medicament and a food product.

4. The method in accordance with claim 1, wherein the composition comprises at least one other kind of other food grade bacteria and/or yeast.

5. The method in accordance with claim 4, wherein the food grade bacteria is selected from the group consisting of lactic acid bacteria, bifidobacteria, propionibacteria and mixtures thereof.

6. The method in accordance with claim 1, wherein the composition contains at least one prebiotic.

7. The method in accordance with claim 6, wherein the prebiotic is selected from the group consisting of oligosaccharides, inulin, dietary fibers, and mixtures thereof.

8. The method in accordance with claim 1, wherein at least a part of the *Lactobacillus helveticus* is alive in the composition.

9. The method in accordance with claim 1, wherein at least a part of the *Lactobacillus helveticus* is not alive in the composition.

10. The method in accordance with claim 1, wherein a daily dose of the composition is administered, and wherein the composition is a medicament comprising between $10^2$ and $10^{12}$ cfu of *Lactobacillus helveticus* CNCM I-4095 per daily dose.

11. The method in accordance with claim 1, wherein the composition is a food product and comprises between $10^3$ and $10^{12}$ cfu of *Lactobacillus helveticus* CNCM I-4095 per g of the dry weight of the food composition.

12. The method in accordance with claim 1 to treat obesity.

13. The method in accordance with claim 1 to reduce caloric intake and/or to increase satiety.

14. The method in accordance with claim 1 to treat metabolic disorders.

15. The method in accordance with claim 1, wherein a daily dose of the composition is administered, and wherein the composition is a medicament and comprises between $10^2$ and $10^{12}$ cells of *Lactobacillus helveticus* CNCM I-4095 per daily dose.

16. The method in accordance with claim 1, wherein the composition is a food product and comprises between $10^3$ and $10^{12}$ cells of *Lactobacillus helveticus* CNCM I-4095 per g of the dry weight of the food composition.

17. A biologically pure culture of *Lactobacillus helveticus* CNCM I-4095.

18. A method for weight maintenance in a mammal in need thereof comprising administering to the mammal a composition comprising an effective amount of *Lactobacillus helveticus* CNCM I-4095.

19. The method in accordance with claim 18, wherein the mammal is a human that is at least 2 years old.

20. The method in accordance with claim 18, wherein the composition is selected from the group consisting of a medicament and a food product.

21. The method in accordance with claim 18, wherein the composition comprises at least one other kind of other food grade bacteria and/or yeast.

22. The method in accordance with claim 18, wherein the food grade bacteria is selected from the group consisting of lactic acid bacteria, bifidobacteria, propionibacteria and mixtures thereof.

23. The method in accordance with claim 18, wherein the composition contains at least one prebiotic.

24. The method in accordance with claim 18, wherein the prebiotic is selected from the group consisting of oligosaccharides, inulin, dietary fibers, and mixtures thereof.

25. The method in accordance with claim 18, wherein at least a part of the *Lactobacillus helveticus* is alive in the composition.

26. The method in accordance with claim 18, wherein at least a part of the *Lactobacillus helveticus* is not alive in the composition.

27. The method in accordance with claim 18, wherein a daily dose of the composition is administered, and wherein the composition is a medicament comprising between $10^2$ and $10^{12}$ cfu of *Lactobacillus helveticus* CNCM I-4095 per daily dose.

28. The method in accordance with claim 18, wherein the composition is a food product and comprises between $10^3$ and $10^{12}$ cfu of *Lactobacillus helveticus* CNCM I-4095 per g of the dry weight of the food composition.

29. The method in accordance with claim 18, to treat obesity.

30. The method in accordance with claim 18, to reduce caloric intake and/or to increase satiety.

31. The method in accordance with claim 18, to treat metabolic disorders.

32. The method in accordance with claim 18, wherein a daily dose of the composition is administered, and wherein the composition is a medicament comprising between $10^2$ and $10^{12}$ cells of *Lactobacillus helveticus* CNCM I-4095 per daily dose.

33. The method in accordance with claim 18, wherein the composition is a food product and comprises between $10^3$ and $10^{12}$ cells of *Lactobacillus helveticus* CNCM I-4095 per g of the dry weight of the food composition.

* * * * *